(12) United States Patent
Hong et al.

(10) Patent No.: US 8,514,218 B2
(45) Date of Patent: Aug. 20, 2013

(54) IMAGE-BASED PATH PLANNING FOR AUTOMATED VIRTUAL COLONOSCOPY NAVIGATION

(75) Inventors: Wei Hong, Edison, NJ (US); Gianluca Paladini, Skillman, NJ (US)

(73) Assignee: Siemens Aktiengesellschaft, Munich (DE)

(*) Notice: Subject to any disclaimer, the term of this patent is extended or adjusted under 35 U.S.C. 154(b) by 1218 days.

(21) Appl. No.: 12/190,912

(22) Filed: Aug. 13, 2008

(65) Prior Publication Data

US 2009/0048482 A1 Feb. 19, 2009

Related U.S. Application Data

(60) Provisional application No. 60/955,669, filed on Aug. 14, 2007.

(51) Int. Cl.
| | |
|---|---|
| *G06T 15/00* | (2011.01) |
| *G06T 15/40* | (2011.01) |
| *G06T 17/00* | (2006.01) |
| *G06K 9/00* | (2006.01) |
| *A61B 5/05* | (2006.01) |

(52) U.S. Cl.
USPC ........... 345/419; 345/421; 345/422; 345/424; 382/128; 382/131; 382/132; 600/411; 600/425; 600/101

(58) Field of Classification Search
None
See application file for complete search history.

(56) References Cited

U.S. PATENT DOCUMENTS

| 6,514,082 | B2 | 2/2003 | Kaufman et al. | |
|---|---|---|---|---|
| 7,081,088 | B2 | 7/2006 | Geiger | |
| 2007/0276228 | A1* | 11/2007 | Vining et al. | 600/425 |
| 2008/0118117 | A1* | 5/2008 | Gauldie et al. | 382/128 |
| 2009/0063118 | A1* | 3/2009 | Dachille et al. | 703/11 |

* cited by examiner

*Primary Examiner* — Tize Ma
(74) *Attorney, Agent, or Firm* — Donald B. Paschburg; F. Chau & Associates, LLC

(57) ABSTRACT

A method for automatic virtual endoscopy navigation, including: (a) using a fisheye camera to generate an endoscopic image and a depth image from a current position of the camera in lumen computed tomographic (CT) data; (b) segmenting a first region and a second region from the depth image, wherein the first region identifies a view direction of the camera and the second region is an area through which the camera can be moved without touching an inner surface of the lumen; (c) moving the camera from the current position, while pointing the camera in the view direction, to a next position in the second region; and (d) repeating steps (a-c) in sequence using the next position in step (c) as the current position in step (a).

23 Claims, 8 Drawing Sheets

(a) Perspective Endoscopic Image (b) Fisheye Endoscopic Image (c) Perspective Depth Image (d) Fisheye Depth Image (a) Fisheye Endoscopic Image (b) Fisheye Depth Image

(c) Target Region

(d) Safe Region

IMAGE-BASED PATH PLANNING FOR AUTOMATED VIRTUAL COLONOSCOPY NAVIGATION

CROSS-REFERENCE TO RELATED APPLICATION

This application claims the benefit of U.S. Provisional Application No. 60/955,669, filed Aug. 14, 2007, the disclosure of which is incorporated by reference herein in its entirety.

BACKGROUND OF THE INVENTION

1. Technical Field

The present invention relates to virtual endoscopy.

2. Discussion of the Related Art

The second leading cause of cancer-related deaths in the United States is colorectal cancer. Unfortunately, it is most often discovered after the patient has developed symptoms. It is recommended that adults should be screened to detect cancer-related polyps. The traditional screening using optical colonoscopy, however, is invasive, expensive, time-consuming, and uncomfortable, and requires an intensive bowel preparation. Because of this, many are not screened. Virtual colonoscopy (VC), also known as computed tomographic colonography (CTC), has been developed to help encourage adults to be regularly screened for polyps. In VC fly-through navigation, it is crucial to generate an optimal camera path for efficient colonic polyp screening. Automatic path planning is required by a VC system because manual planning is difficult and time-consuming due to the complex shape of the human colon. For complete and accurate diagnosis, a planned path should not produce significant blind areas on the colon surface.

There has been a great deal of research on navigation methods for three-dimensional (3D) virtual endoscopy, which can be classified into three categories: manual navigation [M. Gleicher and A. Witkin, "Through the lens camera control", in Proc. ACM SIGGRAPH '92, pp. 331-340, 1992 and R. Turner, F. Balaguer, E. Gobbetti and D. Thalmann, "Physically-based interactive camera motion control using 3D input devices", in Computer Graphics International '91, pp. 135-145, 1991], planned navigation [L. Hong, A. Kaufman, Y. Wei, A Viswambharan, M. Wax, and Z. Liang, "3D virtual colonoscopy", in IEEE Symposium on Biomedical Visualization, pp. 26-32, 1995 and G. Rubin, C. Beaulieu, V. Argiro, H. Ringl, A. Norbash, J. Feller, M. Dake, R. Jeffey, and S. Napel, "Perspective volume rendering of CT and MRI images: Applications for endoscopic imaging", Radiology 99, pp. 321-330, 1996], and guided navigation [L. Hong, S. Muraki, A. Kaufmann, D. Bartz and T. He, "Virtual voyage: Interactive navigation in the human colon", in Proc. ACM SIGGRAPH '97, pp. 27-34, 1997, M. Wan, Q. Tang, A. Kaufman, Z. Liang, and M. Wax, "Volume rendering based interactive navigation within the human colon", in Proc. IEEE Visualization '99, pp. 397-400, 1999 and K. Kwon and B. Shin, "An efficient camera path computation using image-space information in virtual endoscopy", Lecture Notes in Computer Science 3280, pp. 118-125, 2004]. Manual navigation requires the user to control the camera at every step, which is inefficient and uncomfortable. Moreover, the camera may penetrate through the colon surface when it is incorrectly handled by a physician.

Planned navigation calculates entire camera path and orientations in the preprocessing step, then continuously moves the camera along the pre-calculated path during the navigation. In this method, the physician cannot intuitively change the camera position and orientation. Further, a lot of computation is required in the preprocessing step. The centerline of the colon lumen is usually used as the camera path to obtain a wide view of the colonic surface. Topological thinning methods [L. Hong, A. Kaufman, Y. Wei, A Viswambharan, M. Wax, and Z. Liang, "3D virtual colonoscopy", in IEEE Symposium on Biomedical Visualization, pp. 26-32, 1995, D. Paik, C. Beaulieu, R. Jeffery, G. Rubin, and S. Napel, "Automated flight path planning for virtual endoscopy", Medical Physics 25(5), pp. 629-637, 1998, and R. Sadlier and P. Whelan, "Fast colon centerline calculation using optimized 3D topological thinning", Computerized Medical Imaging and Graphics 29, pp. 251-258, 2005] have been used to eliminate the outermost layer of a segmented colon successively with only the centerline voxels remaining. In the distance mapping method, a distance field is computed, and then the minimum cost spanning tree is built to extract the optimal colonic centerline. Bitter et al. [I. Bitter, M. Sato, M. Bender, K. McDonnel, and A. Kaufman, "CEASAR: A smooth, accurate and robust centerline extraction algorithm", in Proc. IEEE Visualization '00, pp. 45-52, 2000] have proposed an efficient centerline algorithm using a penalty distance, which is the combination of the distance from the source and the distance from the boundary. Wan et al. [M. Wan, Z. Liang, Q. Ke, L. Hong, I. Bitter, and A. Kaufman, "Automatic centerline extraction for virtual colonoscopy", IEEE Transactions on Medical Imaging 21(12), pp. 1450-1460, 2002] have used the exact Euclidian distance from each voxel inside the colon lumen to the nearest colon boundary to extract the colon centerline and its associated branches. Hassouna et al. [M. Hassouna and A. Farag, "Robust centerline extraction framework using level sets", in IEEE Computer Vision and Pattern Recognition, pp. 458-465, 2005] have proposed a robust centerline extraction method, introducing a new speed function of level sets. However, all of these methods are computationally expensive, especially when they are applied to volumetric data.

Guided navigation provides some guidance for the navigation and allows the physician to control it when desired. The potential field [L. Hong, S. Muraki, A. Kaufmann, D. Bartz and T. He, "Virtual voyage: Interactive navigation in the human colon", in Proc. ACM SIGGRAPH '97, pp. 27-34, 1997 and M. Wan, Q. Tang, A. Kaufman, Z. Liang, and M. Wax, "Volume rendering based interactive navigation within the human colon", in Proc. IEEE Visualization '99, pp. 397-400, 1999] has been used to determine the camera position and orientation by considering the attractive force directing to the target point, repulsive force from the colon surface, and the external force. It consists of two distance fields inside the colon lumen: distance from the colonic surface and distance from the target point of the current navigation. This method requires additional storage for distance fields, and the computation of the potential field is time consuming. Kang et al. [D. Kang and J. Ra, "A new path planning algorithm for maximizing visibility in computed tomography colonography", IEEE Transactions on Medical Imaging 24(8), pp. 957-968, 2005] have proposed a method to determine view positions and their view directions to minimize the blind areas during navigation. However, this algorithm showed poor performance to minimize the blind area between haustral folds although the visible areas at the curved regions are increased. Kwon et al. [K. Kwon and B. Shin, "An efficient camera path computation using image-space information in virtual endoscopy", Lecture Notes in Computer Science 3280, pp. 118-125, 2004] have used image space information generated in rendering time to determine the camera position and direction. This technique does not require preprocessing or extra storage, but it is highly likely to converge to local minima in complex regions.

SUMMARY OF THE INVENTION

In an exemplary embodiment of the present invention, a method for automatic virtual endoscopy navigation, comprises: (a) using a fisheye camera to generate an endoscopic image and a depth image from a current position of the camera in lumen computed tomographic (CT) data; (b) segmenting a first region and a second region from the depth image, wherein the first region identifies a view direction of the camera and the second region is an area through which the camera can be moved without touching an inner surface of the lumen; (c) moving the camera from the current position, while pointing the camera in the view direction, to a next position in the second region; and (d) repeating steps (a-c) in sequence using the next position in step (c) as the current position in step (a).

The method further comprises displaying the endoscopic image to visualize the movement of the camera. The method further comprises identifying a polyp in the lumen in the displayed image.

The fisheye camera has up to a 360 degree field of view.

The current position of the camera is initially a seed point that is placed in the lumen CT data by a medical practitioner.

The method steps for virtual endoscopy navigation are performed immediately after the lumen CT data is received from a CT scanner.

A region growing method is used to segment the second region and the segmented first region is used as a seed for the region growing.

The method further comprises calculating a centroid of the first region and the second region, respectively, wherein when the camera is moved from the current position to the second position it is moved along a ray toward the centroid of the second region, while being pointed to the centroid of the first region.

The method further comprises calculating a view up vector of the camera and restricting the view direction of the camera by the view up vector to smooth the virtual endoscopy navigation.

The next position is a point between the current position and a center of the segmented second region. Step (d) is performed when the camera is approaching the next position or when the camera reaches the next position.

The lumen is a colon.

In an exemplary embodiment of the present invention, a system for automatic virtual endoscopy navigation, comprises: a memory device for storing a program; a processor in communication with the memory device, the processor operative with the program to: (a) use a fisheye camera to generate an endoscopic image and a depth image from a current position of the camera in lumen CT data; (b) segment a first region and a second region from the depth image, wherein the first region identifies a view direction of the camera and the second region is an area through which the camera can be moved without touching an inner surface of the lumen; (c) move the camera from the current position, while pointing the camera in the view direction, to a next position in the second region; and (d) repeat steps (a-c) in sequence using the next position in step (c) as the current position in step (a).

The processor is further operative with the program to display the endoscopic image to visualize the movement of the camera. The processor is further operative with the program to identify a polyp in the lumen in the displayed image.

The fisheye camera has up to a 360 degree field of view.

The current position of the camera is initially a seed point that is placed in the lumen CT data by a medical practitioner.

The processor is further operative with the program code to execute the virtual endoscopy navigation immediately after the lumen CT data is received from a CT scanner.

A region growing method is used to segment the second region and the segmented first region is used as a seed for the region growing.

The processor is further operative with the program to calculate a centroid of the first region and the second region, respectively, wherein when the camera is moved from the current position to the second position it is moved along a ray toward the centroid of the second region, while being pointed to the centroid of the first region.

The processor is further operative with the program to calculate a view up vector of the camera and restrict the view direction of the camera by the view up vector to smooth the virtual endoscopy navigation.

The next position is a point between the current position and a center of the segmented second region. Step (d) is performed when the camera is approaching the next position or when the camera reaches the next position.

The lumen is a colon.

In an exemplary embodiment of the present invention, a computer readable medium tangibly embodying a program of instructions executable by a processor to perform method steps for automatic virtual endoscopy navigation is provided, the method steps comprising: (a) using a fisheye camera to generate an endoscopic image and a depth image from a current position of the camera in lumen CT data; (b) segmenting a first region and a second region from the depth image, wherein the first region identifies a view direction of the camera and the second region is an area through which the camera can be moved without touching an inner surface of the lumen; (c) moving the camera from the current position, while pointing the camera in the view direction, to a next position in the second region; and (d) repeating steps (a-c) in sequence using the next position in step (c) as the current position in step (a).

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

In this disclosure, we present an automatic image-based path planning algorithm for virtual endoscopy (VE) fly-through navigation, in accordance with an exemplary embodiment of the present invention. In our method, preprocessing is not required, and camera position and orientation are calculated on-the-fly using rendered depth images. The only input of our algorithm is lumen computed tomographic (CT) data and a seed point provided by a physician. Therefore, the VE fly-through navigation can be performed immediately after the lumen data are loaded from a computer's hard drive.

In the following description, our VE method/system will be referred to as a virtual colonoscopy (VC) method/system, since the lumen referenced hereinafter is a colon. The present invention is not limited thereto. For example, our VE method applies equally well to other lumens such as, bronchi and blood vessels, etc.

1. Methodology

Figure 1:
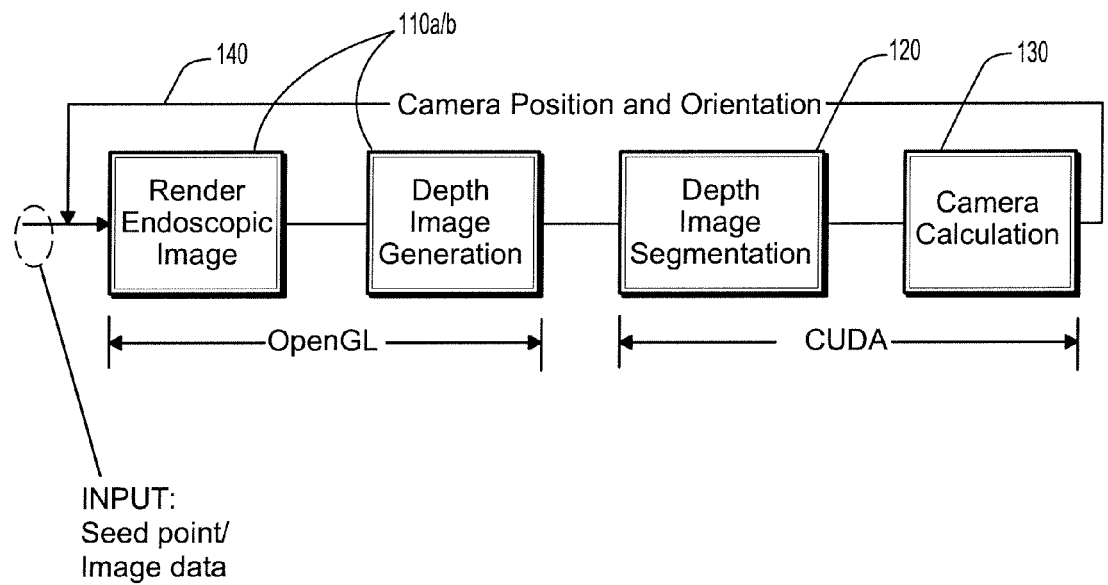
FIG. 1 is an overview of an image-based navigation method in accordance with an exemplary embodiment of the present invention.

In a VC fly-through navigation system, the path planning algorithm is required to provide camera positions and orientations to a rendering engine. In order to obtain a wide view of the colonic surface, the camera should stay as far away from the surface as possible. The centerline of the colon lumen is not used as the camera path, because its processing is time-consuming and we want to generate the camera path on-the-fly during the navigation. However, we still need to keep the camera away from the colonic surface to achieve better visibility coverage during the navigation. In our method, depth maps are used to determined the camera positions and orientations. Our method consists of three steps: depth image generation (110a/b), depth image segmentation (120), and camera calculation (130). Steps 110a/b-130 are repeated for a next position of the camera (140). The overview of our image-based navigation method is shown in FIG. 1.

1.1 Depth Image Generation

In Kwon et al.'s method [K. Kwon and B. Shin, "An efficient camera path computation using image-space information in virtual endoscopy", Lecture Notes in Computer Science 3280, pp. 118-125, 2004], camera orientation for the next frame is determined using a ray that has maximum distance in the current frame, and camera position in the next frame is calculated using the center of gravity of an organ region on a cross-sectional image. However, the camera is highly likely to converge to local minima in complex regions. In our method, we use a wide angle fisheye camera to generate a depth image at the current frame and then segment the depth image to provide spatial information of the colon lumen for calculating camera position and orientation for the next frame. By using an angular fisheye lens, larger view port angles can be achieved in the final image. This is helpful to solve the local convergence problem and improve the performance of the VC system.

Figure 2:
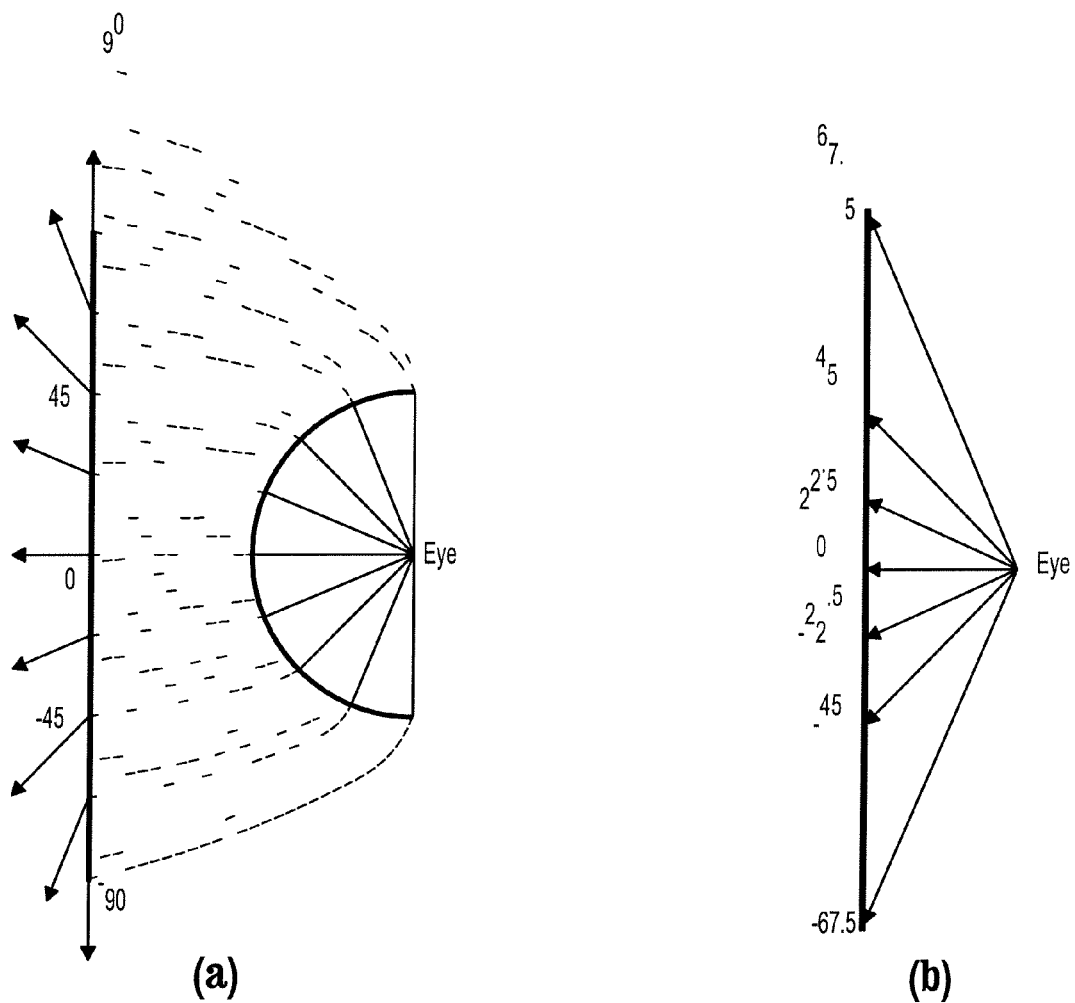
FIG. 2 is an illustration of (a) a 180 degree angular fisheye projection, and (b) a 135 degree perspective projection.

The fisheye lens is a specially designed lens which achieves wider viewing angles. An angular fisheye projection [P. Bourke, "Computer generated angular fisheye projections", 2001.] is defined so that the distance from the center of the image is proportional to the angle from the camera view direction as shown in FIG. 2(a). There are two major differences between angular fisheye projection and perspective projection (see FIG. 2). First, in an angular fisheye image the resolution is approximately equal across the whole image. Second, an angular fisheye projection can be used for angles all the way up to a full 360 degrees. In this way, the physician has more chances to see potential abnormal anatomical structures, such as polyps. Further, since the angular fisheye camera is an ideal lens, it provides images with less distortion than those captured with a real fisheye lens used by an endoscope.

The ray direction corresponding to any pixel on the image plane can be calculated using a special transformation from pixel coordinates to three dimensional (3D) polar coordinates, as described in [P. Bourke, "Computer generated angular fisheye projections", 2001.]. First, the image coordinates are transformed from pixel coordinates (i,j) into normalized coordinates (x,y) ranging from −1 to 1 using the following equation, assuming the resolution of the image plane is (w,h).

$$\begin{cases} x = (2i+1)/w - 1; \\ y = (2j+1)/h - 1; \end{cases} \quad (1)$$

Next, the 3D polar coordinates (r,φ,θ) are calculated as:

$$\begin{cases} r = sqrt(x*x + y*y); \\ \phi = a\tan(y/x); \\ \theta = r*\delta/2; \end{cases} \quad (2)$$

where the angle θ is r multiplied by half the intended fisheye angle δ which may be anything up to 360 degrees, and 0≦r≦1. Any pixels where r>1 are ignored, which are shown in black in our implementation. 3D polar coordinates can then be easily transformed in 3D Cartesian coordinates. Note that the images captured with a real fisheye lens such as an endoscope will have other distortions to the ideal fisheye lens described here. From the above equations, we can see that the described transformation is only related to pixel coordinates and image resolution. Thus, we can pre-compute the transformation between pixel coordinates and 3D Cartesian coordinates and store the result in a 2D texture to improve performance.

Figure 3A:
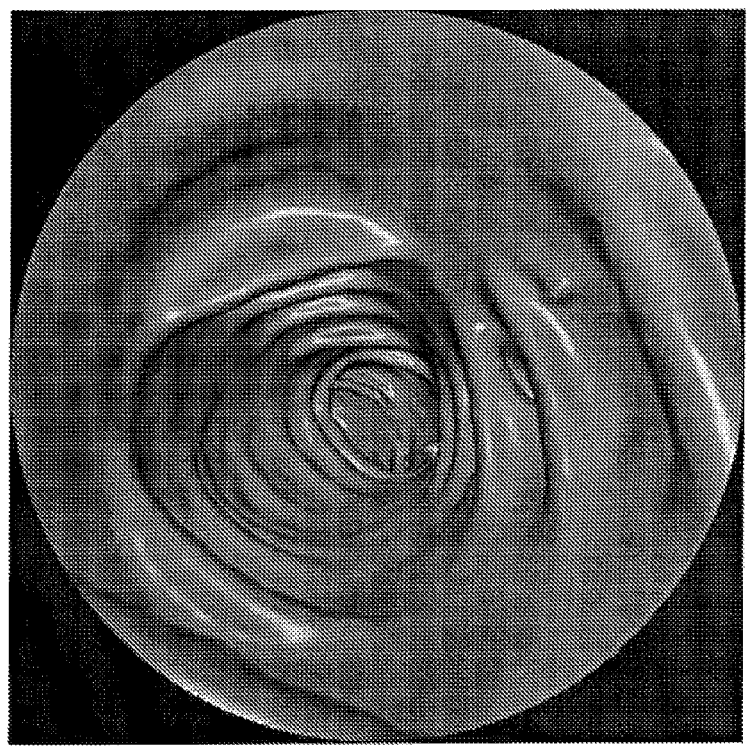
FIGS. 3A and 3B show comparisons between perspective projection and fisheye projection.
Figure 3A:
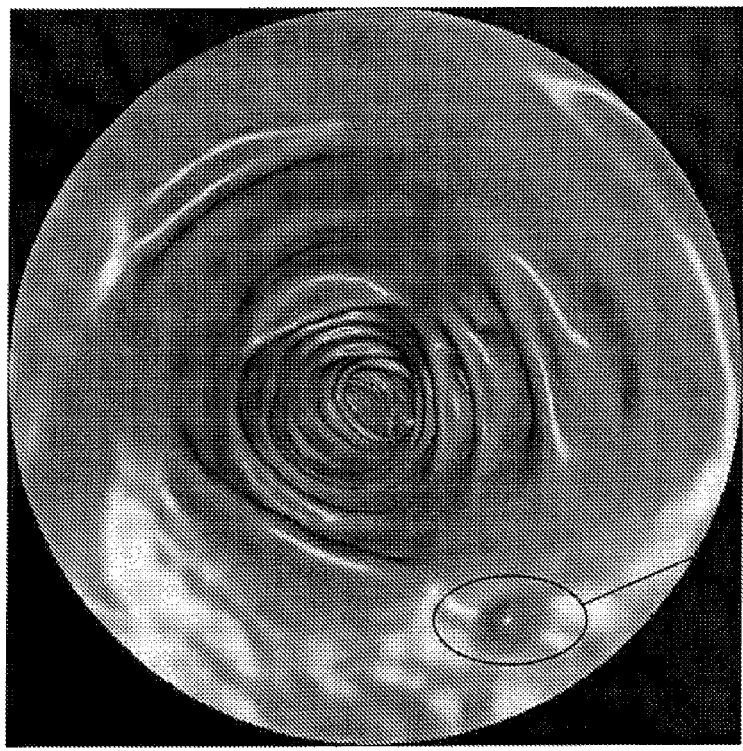
Figure 3B:
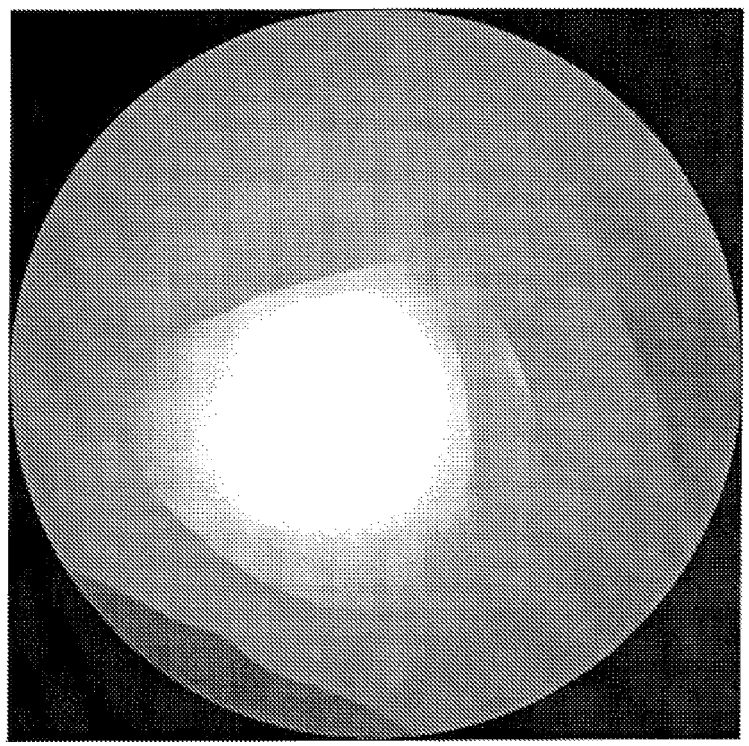
Figure 3B:
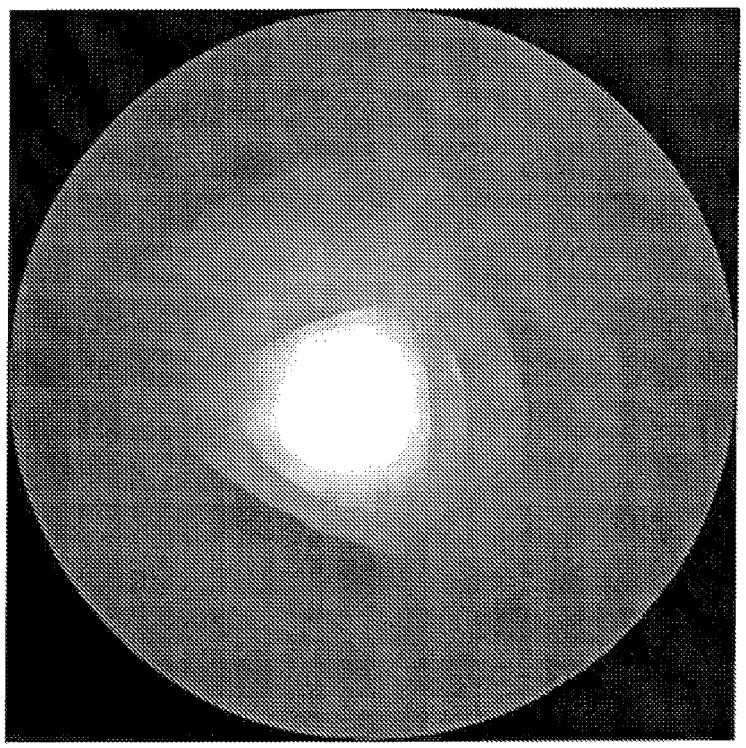

Our depth image generation algorithm is based on a ray casting volume rendering scheme implemented on a graphics processing unit (GPU). See [J. Kruger and R. Westermann, "Acceleration techniques for gpu-based volume rendering", in Proc. IEEE Visualization '03, pp. 287-292, 2003] for a description of such a scheme. For each pixel, its 3D ray direction is calculated using the above transformation. Then, a ray is cast into the volume data to do regular volume rendering integral. When the ray is terminated, it returns a depth value instead of color information. A depth image using our algorithm is shown in FIG. 3B(d).

In order to obtain better visibility coverage and less distortion, a 90 degree perspective projection is usually used in VC systems, see e.g., [L. Hong, S. Muraki, A. Kaufmann, D. Bartz and T. He, "Virtual voyage: Interactive navigation in the human colon", in Proc. ACM SIGGRAPH '97, pp. 27-34, 1997 and M. Wan, Q. Tang, A. Kaufman, Z. Liang, and M. Wax, "Volume rendering based interactive navigation within the human colon", in Proc. IEEE Visualization '99, pp. 397-400, 1999]. Compared with a normal perspective projection, more information can be obtained with less distortion when an angular fisheye projection is used. In FIGS. 3A and 3B, comparisons between a 90 degree perspective projection and a 180 degree angular fisheye projection are shown using both endoscopic images and depth images. Comparing the generated endoscopic images, we can see that a small polyp is shown in the fisheye endoscopic image (FIG. 3A(b)), which is not shown in the perspective endoscopic image (FIG. 3A(a)). Similarly, the fisheye depth image (FIG. 3B(d)) provides more information about the colon lumen than the perspective depth image (FIG. 3B(c)) does.

1.2 Depth Image Segmentation

The depth image generated using angular fisheye projection provides the spatial information about the colon lumen in front of the camera. The colon haustral folds can be detected in the depth image using edge detection algorithms, such as those described in [M. Nixon and A. Aguado, Feature Extraction and Image Processing, ELSEVIER, Amsterdam, The Netherlands, 2002]. The centers of these haustral folds are useful landmarks to guide the camera. It is recommended to move the camera passing through the centers of these curved contours during the navigation. However, it is difficult to accurately detect these haustral folds in several milliseconds even when the latest GPU is used. Thus, in our current implementation we only use the thresholding algorithm to segment the depth image.

Figure 4A:
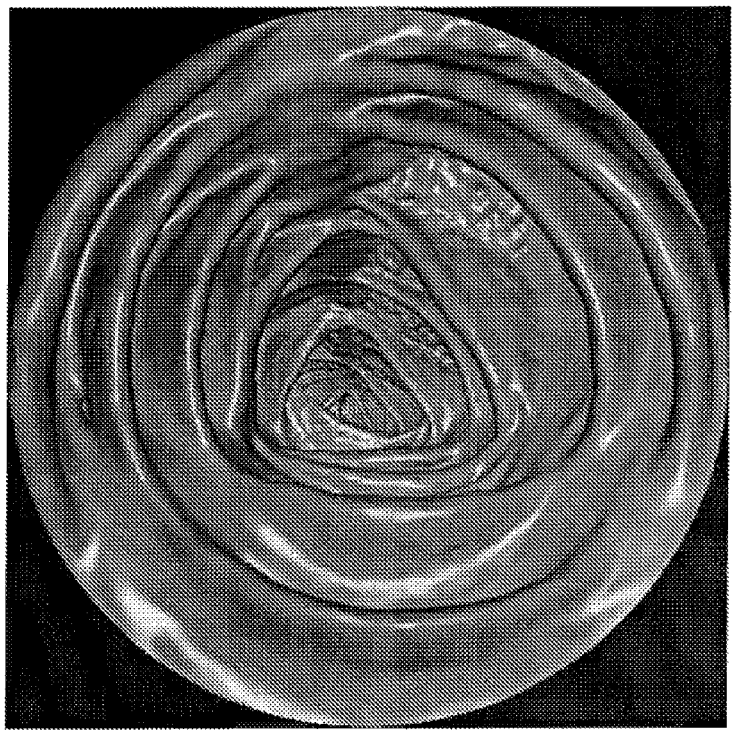
FIGS. 4A and 4B illustrate depth image segmentation in accordance with an exemplary embodiment of the present invention.
Figure 4A:
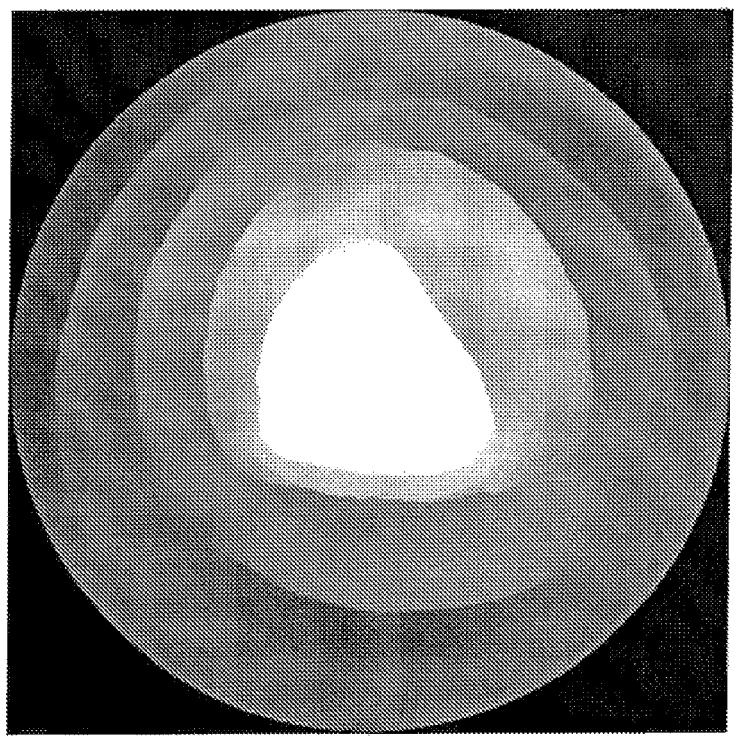
Figure 4B:
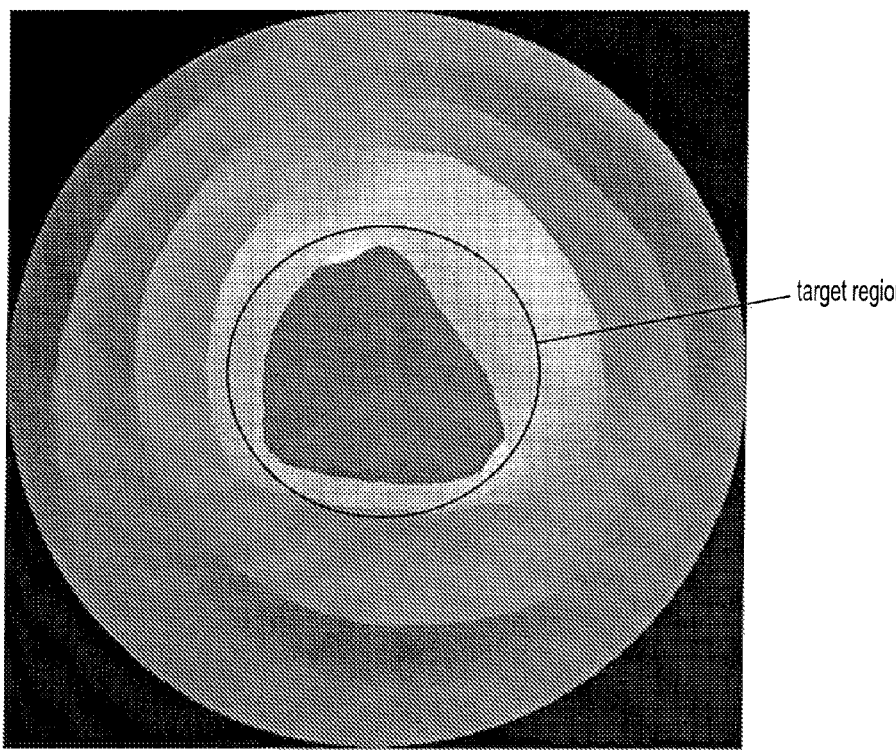
Figure 4B:
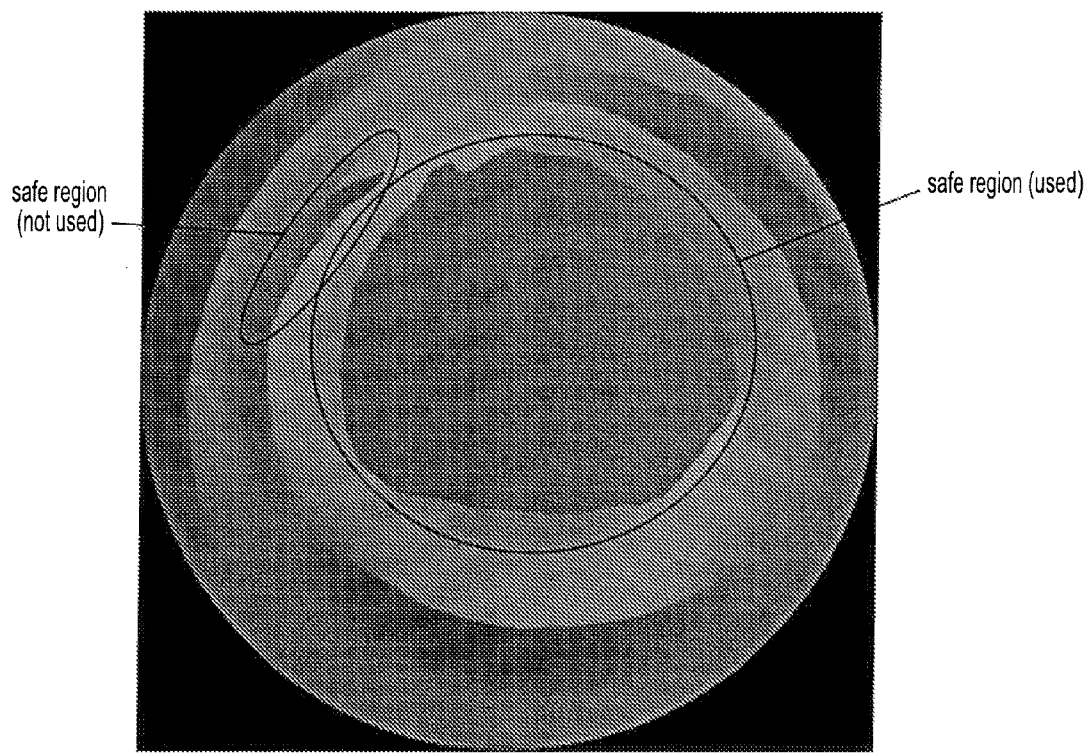

In FIG. 4A(a), a fisheye endoscopic image is displayed to show the complex structure of the human colon, its corresponding depth image is shown in FIG. 4A(b). In the depth image, the gray level is proportional to the distance from the camera to the colon surface. The brighter region corresponds to the colon lumen which is far away from the current camera location, called target region (see circled region in FIG. 4B(c)). The center of this region can be used to determine the view direction of the camera. The target region can be efficiently detected in the depth image using a pre-defined distance value. Similarly, we can segment the depth image using a smaller distance value (see circled regions in FIG. 4B(d)), which provides the spatial information to guide the camera. This region is called safe region, which means moving the camera towards the center of this region is safe. It is noted that sometimes the safe region is separated as shown in FIG. 4B(d). In this case, we only use the region that contains the target region to guide the camera. Thus, we use a region growing method to segment a safe region using the segmented target region as the seed.

1.3 Camera Calculation

In this section, we describe a method to move the camera and setup the view direction of the camera based on the segmented depth image. Each pixel on the image plane corresponds to a ray direction in the 3D Cartesian coordinates. After the target region and the safe region are segmented from the current depth image, their centroid is calculated respectively, which is used to access its corresponding ray direction. We then move the camera from the current position along the ray direction corresponding to the centroid of the safe region. Moreover, the camera is pointed to the centroid of the segmented target region.

In order to minimize the rotation between the consecutive endoscopic views to provide a user comfortable navigation, the following equation is used to calculate the view up vector of the camera:

$$u_i = u_{i-1} - (u_{i-1} \cdot v_i) v_i \quad (3)$$

where $u_i$ is the view up vector and $v_i$ is the view direction at the current camera position. A detailed description of equation (3) can be found in [D. Kang and J. Ra, "A new path planning algorithm for maximizing visibility in computed tomography colonography", IEEE Transactions on Medical Imaging 24(8), pp. 957-968, 2005].

2. Implementation and Results

We have implemented and tested our method using a workstation with two 2.0 GHz Intel Xeon central processing units (CPUs), 2 GB memory and an NVIDIA Geforce 8800GTX graphics card with 768 MB memory. Our method has been applied to 20 clinical data sets randomly selected from WRAMC VC data at National Cancer Institute at NIH.

An important thing about our implementation is that the depth image should not be read back from the GPU, because reading data back causes Open Graphics Library (OpenGL) pipeline stalls and inhibits parallelism on the current graphics card. NVIDIA's Compute Unified Device Architecture (CUDA) [NVIDIA, "Cuda programming guide", 2007.] is a new hardware and software architecture for issuing and managing computations on the GPU as a data-parallel computing device without the need of mapping them to a graphics application programming interface (API). Our depth image generation algorithm is implemented using the OpenGL shader program. OpenGL buffer objects can be mapped into the address space of CUDA, either to enable CUDA to read data written by OpenGL or to enable CUDA to write data for consumption by OpenGL. Thus, we have implemented our depth image segmentation algorithms using CUDA, which has two obvious advantages:

1. There is no data transfer between CPU and GPU. The low performance readback from the GPU to the CPU is avoided.
2. The depth image segmentation algorithms are performed on the GPU in parallel, which is much more efficient than that on the CPU.

Moreover, we do not need to segment the target region and the safe region for every frame during the fly-through navigation. We only perform this operation when the center of the last segmented safe region is approached. In our VC system, the endoscopic view is rendered with a resolution of 512×512 using a volume ray casting algorithm. Either angular fisheye projection or perspective projection can be used to render the endoscopic view. If the angular fisheye projection is used, the endoscopic image and depth image can be rendered using a single shader program to improve the overall performance. The average timings for each step of our image-based path planning method are listed in Table 1. Because of our CUDA implementation of the depth image segmentation algorithm, our VC system can still guarantee 30 frame per second (FPS) during the fly-through navigation.

TABLE 1

Average timings for each step of our VC system.

| Step | Execution Time |
|---|---|
| Endoscopic Image Rendering | 9.5 ms |
| Depth Image Generation | 2.8 ms |
| Depth Image Segmentation | 7.4 ms |
| Camera Calculation | <1 ms |
| Total | <20.7 ms |

Figure 5:
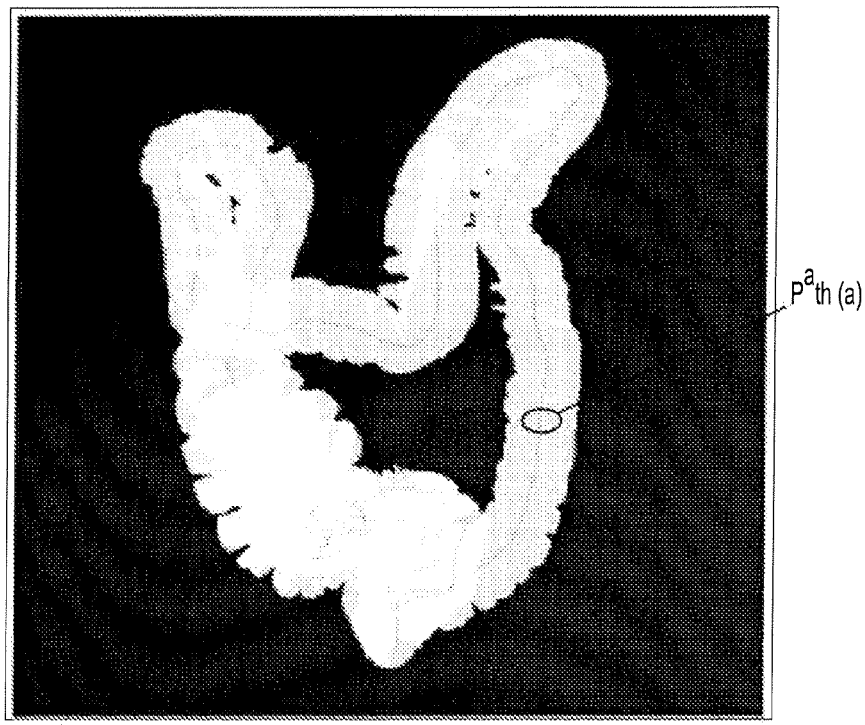
FIG. 5 shows two camera paths generated using the image-based navigation method in accordance with an exemplary embodiment of the present invention.
Figure 5:
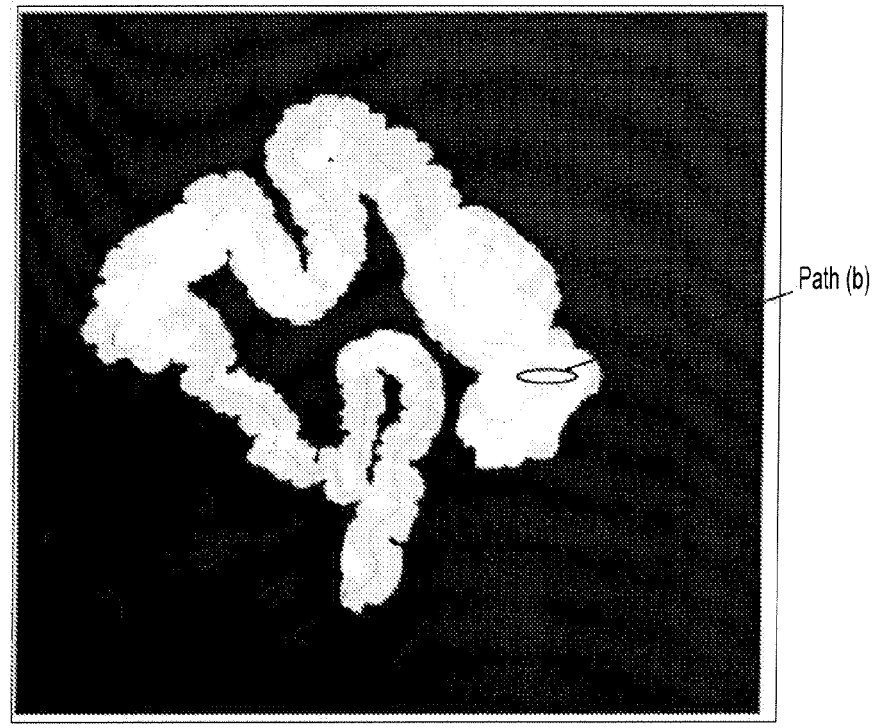

Although our image-based path planning algorithm does not require preprocessing, our system still requires the physician to provide a starting point. We recommend that the physician provides a point around the rectum. FIG. 5 shows two camera paths generated using our path planning algorithm starting from the rectum. It is noted that the camera is always located at the center of the colon lumen to obtain a wide view during the fly-through navigation.

3. Conclusions

We have described an efficient image-based path planning method for automated VC fly-through navigation. It does not require preprocessing and extra storage, which allows the physician to start inspection right after the data are ready. A 180 degree angular fisheye lens is used to generate a depth image based on a ray casting volume rendering scheme. It can capture more information than the perspective projection, which is widely used in the rendering of virtual colonoscopy applications. Our method uses an image segmentation algorithm to detect safe regions and target regions from the rendered depth images, which are then used to determine camera positions and orientations on-the-fly. Our method was applied to 20 colon data sets. The experimental results showed that the generated path was located in the center of the colon lumen for an effective polyp screening. It also increased the user comfort during the virtual colonoscopy navigation.

A system in which exemplary embodiments of the present invention may be implemented will now be described with reference to FIG. 6.

Figure 6:
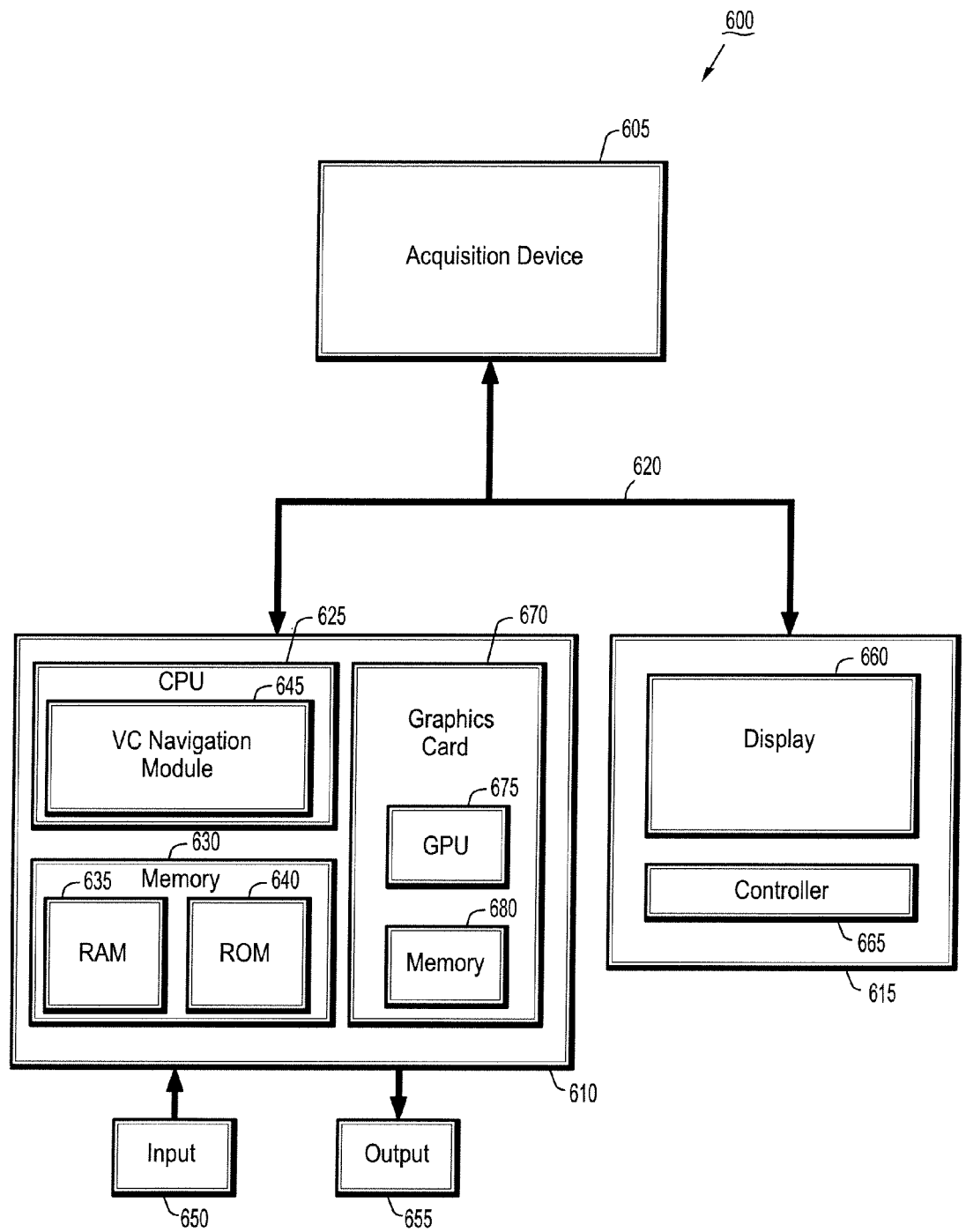
FIG. 6 is block diagram of a system in which exemplary embodiments of the present invention may be implemented.

In FIG. 6, the system 600 includes an acquisition device 605, a computer 610 and an operator's console 615 connected over a wired or wireless network 620. The acquisition device 605 may be a CT imaging device or any other 3D high-resolution imaging device such as a magnetic resonance (MR) scanner or ultrasound scanner.

The computer 610, which may be a portable or laptop computer, a medical diagnostic imaging system or a picture archiving communications system (PACS) data management station, includes a CPU 625, a memory 630 and a graphics card 670 which are connected to an input device 650 and an output device 655. The CPU 625 includes a VC navigation module 645 that includes software for executing methods in accordance with exemplary embodiments of the present invention. Although shown inside the CPU 625, the VC navigation module 645 can be located in the graphics card 670 or external to the CPU 625, for example.

The memory 630 includes a random access memory (RAM) 635 and a read-only memory (ROM) 640. The memory 630 can also include a database, disk drive, tape drive, etc., or a combination thereof. The RAM 635 functions as a data memory that stores data used during execution of a program in the CPU 625 and is used as a work area. The ROM 640 functions as a program memory for storing a program executed in the CPU 625. The input 650 is constituted by a keyboard, mouse, etc., and the output 655 is constituted by a liquid crystal display (LCD), cathode ray tube (CRT) display, printer, etc.

The graphics card 670, which is used to take binary data from the CPU 625 and turn it into an image, includes a GPU 675 and a memory 680. In order to achieve real-time rendering, the depth image segmentation is performed on the GPU 675. The GPU 675 determines what to do with each pixel to be displayed, for example, on the output device 655 or a display 660 of the operator's console 615. In operation, the GPU 675 makes a 3D image by first creating a wire frame out of straight lines, rasterizing the image and adding lighting, texture and color to the 3D image. The memory 680, which may be a RAM, holds information regarding each pixel and temporarily stores completed images. Although not shown, the graphics card 670 also includes a connection to a motherboard, which also holds the CPU 625, for receiving data and power and a connection to the output device 655 for outputting the picture. The memory 680 could be included in the GPU 675 or the GPU 675 could include its own memory for performing storage tasks.

The operation of the system 600 can be controlled from the operator's console 615, which includes a controller 665, e.g., a keyboard, and a display 660. The operator's console 615 communicates with the computer 610 and the acquisition device 605 so that image data collected by the acquisition device 605 can be rendered by the computer 610 and viewed on the display 660. The computer 610 can be configured to operate and display information provided by the acquisition device 605 absent the operator's console 615, by using, e.g., the input 650 and output 655 devices to execute certain tasks performed by the controller 665 and display 660.

The operator's console 615 may further include any suitable image rendering system/tool/application that can process digital image data of an acquired image dataset (or portion thereof) to generate and display images on the display 660. More specifically, the image rendering system may be an application that provides rendering and visualization of medical image data, and which executes on a general purpose or specific computer workstation. The computer 610 can also include the above-mentioned image rendering system/tool/application.

It is to be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It should also be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is to be further understood that the above description is only representative of illustrative embodiments. For convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for automatic virtual endoscopy navigation, comprising:
    (a) using a fisheye camera to generate an endoscopic image and a depth image from a current position of the camera in lumen computed tomographic (CT) data;
    (b) segmenting a first region and a second region from the depth image, wherein the first region identifies a view direction of the camera and the second region is an area through which the camera can be moved without touching an inner surface of the lumen;

(c) moving the camera from the current position, while pointing the camera in the view direction, to a next position in the second region; and (d) repeating steps (a-c) in sequence using the next position in step (c) as the current position in step (a), wherein steps (a-d) are repeatedly performed to move the camera through the lumen, wherein the lumen has a plurality of bends such that the camera travels in opposite directions in different parts of the lumen, wherein the only input is a seed point identifying the current position of the camera the first time step (a) is performed and the CT data.

2. The method of claim 1, further comprising:
displaying the endoscopic image to visualize the movement of the camera.

3. The method of claim 2, further comprising:
identifying a polyp in the lumen in the displayed image.

4. The method of claim 1, wherein the fisheye camera has up to a 360 degree field of view.

5. The method of claim 1, wherein the method steps for virtual endoscopy navigation are performed immediately after the lumen CT data is received from a CT scanner.

6. The method of claim 1, wherein a region growing method is used to segment the second region and the segmented first region is used as a seed for the region growing.

7. The method of claim 1, further comprising:
calculating a centroid of the first region and the second region, respectively,
wherein when the camera is moved from the current position to the second position it is moved along a ray toward the centroid of the second region, while being pointed to the centroid of the first region.

8. The method of claim 7, further comprising:
calculating a view up vector of the camera and restricting the view direction of the camera by the view up vector to smooth the virtual endoscopy navigation.

9. The method of claim 7, wherein the next position is a point between the current position and a center of the segmented second region.

10. The method of claim 9, wherein step (d) is performed when the camera is approaching the next position or when the camera reaches the next position.

11. The method of claim 1, wherein the lumen is a colon.

12. A system for automatic virtual endoscopy navigation, comprising:
a memory device for storing a program;
a processor in communication with the memory device, the processor operative with the program to:
(a) use a fisheye camera to generate an endoscopic image and a depth image from a current position of the camera in lumen computed tomographic (CT) data;
(b) segment a first region and a second region from the depth image, wherein the first region identifies a view direction of the camera and the second region is an area through which the camera can be moved without touching an inner surface of the lumen;
(c) move the camera from the current position, while pointing the camera in the view direction, to a next position in the second region; and
(d) repeat steps (a-c) in sequence using the next position in step (c) as the current position in step (a),
wherein steps (a-d) are repeatedly performed to move the camera through the lumen,
wherein the lumen has a plurality of bends such that the camera travels in opposite directions in different parts of the lumen,
wherein the only input is a seed point identifying the current position of the camera the first time step (a) is performed and the CT data.

13. The system of claim 12, wherein the processor is further operative with the program to:
display the endoscopic image to visualize the movement of the camera.

14. The system of claim 13, wherein the processor is further operative with the program to:
identify a polyp in the lumen in the displayed image.

15. The system of claim 12, wherein the fisheye camera has up to a 360 degree field of view.

16. The system of claim 12, wherein the processor is further operative with the program to execute the virtual endoscopy navigation immediately after the lumen CT data is received from a CT scanner.

17. The system of claim 12, wherein a region growing method is used to segment the second region and the segmented first region is used as a seed for the region growing.

18. The system of claim 12, wherein the processor is further operative with the program to:
calculate a centroid of the first region and the second region, respectively,
wherein when the camera is moved from the current position to the second position it is moved along a ray toward the centroid of the second region, while being pointed to the centroid of the first region.

19. The system of claim 18, wherein the processor is further operative with the program to:
calculate a view up vector of the camera and restrict the view direction of the camera by the view up vector to smooth the virtual endoscopy navigation.

20. The system of claim 18, wherein the next position is a point between the current position and a center of the segmented second region.

21. The system of claim 20, wherein step (d) is performed when the camera is approaching the next position or when the camera reaches the next position.

22. The system of claim 12, wherein the lumen is a colon.

23. A non-transitory computer readable medium tangibly embodying a program of instructions executable by a processor to perform method steps for automatic virtual endoscopy navigation, the method steps comprising:
(a) using a fisheye camera to generate an endoscopic image and a depth image from a current position of the camera in lumen computed tomographic (CT) data;
(b) segmenting a first region and a second region from the depth image, wherein the first region identifies a view direction of the camera and the second region is an area through which the camera can be moved without touching an inner surface of the lumen;
(c) moving the camera from the current position, while pointing the camera in the view direction, to a next position in the second region; and
(d) repeating steps (a-c) in sequence using the next position in step (c) as the current position in step (a),
wherein steps (a-d) are repeatedly performed to move the camera through the lumen,
wherein the lumen has a plurality of bends such that the camera travels in opposite directions in different parts of the lumen,
wherein the only input is a seed point identifying the current position of the camera the first time step (a) is performed and the CT data.

* * * * *